United States Patent [19]
Alper et al.

[11] Patent Number: 4,568,770
[45] Date of Patent: Feb. 4, 1986

[54] PROCESS FOR THE CONVERSION OF A TERMINAL CARBON-CARBON DOUBLE BOND OF AN OLEFINIC HYDROCARBON TO CARBONYL GROUPS

[75] Inventors: Howard Alper; Krzysztof R. Januszkiewicz, both of Ottawa, Canada; David J. H. Smith, Camberley, England

[73] Assignee: The British Petroleum Company p.l.c., London, England

[21] Appl. No.: 536,884

[22] Filed: Sep. 28, 1983

[30] Foreign Application Priority Data

Sep. 30, 1982 [GB] United Kingdom ................. 8227971
Sep. 30, 1982 [GB] United Kingdom ................. 8227973

[51] Int. Cl.$^4$ ............................................. C07C 45/34
[52] U.S. Cl. ..................................... 568/401; 568/360
[58] Field of Search ....................... 568/400, 360, 401

[56] References Cited

U.S. PATENT DOCUMENTS

| | | | |
|---|---|---|---|
| 3,131,223 | 4/1964 | Smidt et al. | 568/401 |
| 3,154,586 | 10/1964 | Bander et al. | 568/401 |
| 4,152,354 | 5/1979 | Stapp | 568/401 |
| 4,203,927 | 5/1980 | Stapp | 568/401 |
| 4,220,604 | 9/1980 | Stapp | 568/401 |
| 4,271,320 | 6/1981 | Tokitoh et al. | 568/401 |
| 4,419,525 | 12/1983 | Shioyama et al. | 568/401 |
| 4,434,082 | 2/1984 | Nurtha et al. | 568/401 |

Primary Examiner—James H. Reamer
Attorney, Agent, or Firm—Brooks, Haidt, Haffner & Delahunty

[57] ABSTRACT

Terminal carbon-carbon double bonds of olefinic hydrocarbons are converted to carbonyl groups by reacting the olefin with oxygen in the presence of (a) a catalyst comprising (i) one or more of the metals palladium, rhodium, ruthenium or iridium, and (ii) copper, (b) a diluent comprising two liquid phases, and (c) a surfactant, provided that when the metal is palladium no alkali or alkaline earth metal is present and the surfactant is dodecyltrimethylammonium or cetyltrimethylammonium chloride or bromide.

13 Claims, No Drawings

PROCESS FOR THE CONVERSION OF A TERMINAL CARBON-CARBON DOUBLE BOND OF AN OLEFINIC HYDROCARBON TO CARBONYL GROUPS

The present invention relates to a process for the conversion of a terminal carbon-carbon double bond of an olefinic hydrocarbon to carbonyl groups by reacting the olefin with oxygen in the presence of (a) a catalyst comprising (i) a metal (ii) copper, (b) a diluent comprising at least two liquid phases, and (c) a surfactant.

European patent application publication No. 0000143 (Phillips Petroleum Company) describes and claims a process for the conversion of the olefinic carbon-carbon double bonds of an olefinic hydrocarbon reactant to carbonyl groups characterised by contacting under reaction conditions under such temperature and pressure conditions that the oxidation of the olefinic reactant takes place, the following components in a reaction system:

(a) oxygen
(b) a diluent comprising at least two liquid phases wherein at least one liquid phase is an aqueous phase
(c) a catalyst consisting essentially of
   (1) palladium
   (2) copper
   (3) an alkali metal or alkaline earth metal chloride; and
(d) a surfactant selected from the group of:
   (1) quaternary ammonium salts of the general formula $(R^{111})_4N^+X^-$,
   (2) alkali metal alkyl sulphates of the general formula $R^{1v}OSO_3M$,
   (3) alkali metal salts of alkanoic acids of the general formula $R^{1v}CO_2M$,
   (4) alkali metal salts of alkaryl sulphonic acids of the general formula:

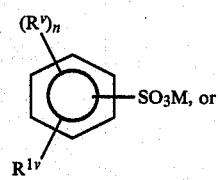

(5) 1-alkyl pyridinium salts of the general formula:

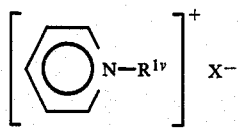

wherein $R^{111}$ is an alkyl radical of from 1 to 20 carbon atoms and wherein the total number of carbon atoms in said quaternary ammonium salt is from about 8 to about 30 carbon atoms; $X^-$ is selected from the group consisting of $Br^-$, $Cl^-$, $I^-$, $F^-$, $R^{111}CO_2^-$, $QSO_3^-$, $BF_4^-$, $HSO_4^-$ wherein Q is an aryl or alkaryl radical of 6 to 10 carbon atoms; $R^{1v}$ is an alkyl radical of from 10 to about 20 carbon atoms; M is an alkali metal; $R^v$ is an alkyl radical of 1 to 4 carbon atoms and wherein n is 0 or an integer of from 1 to 4; and (e) an olefinic hydrocarbon reactant.

We have now found alternative catalysts which are effective under mild conditions for effecting the conversion of a terminal carbon-carbon double bond of an olefin hydrocarbon to carbonyl groups.

Accordingly, the present invention provides a process for the conversion of a terminal carbon-carbon double bond of an olefinic hydrocarbon to carbonyl groups by reacting the olefin with oxygen in the presence of:

(a) a catalyst comprising
   (i) a metal
   (ii) copper
(b) a diluent comprising at least two liquid phases,
(c) a surfactant characterised in that the metal component (i) of the catalyst (a) is one or more of palladium, rhodium, ruthenium or iridium, provided that when the metal is palladium, an alkali metal or alkaline earth metal chloride does not form a component of the catalyst (a) and the surfactant is either dodecyltrimethylammonium chloride or bromide or cetyltrimethylammonium chloride or bromide.

The terminal olefinic hydrocarbon may suitably be an acyclic olefin containing from 3 to 20 carbon atoms per molecule and having either 1, 2 or 3 terminal olefinic carbon-carbon double bonds per molecule, provided that when there are 2 or more terminal carbon-carbon double bonds at least one of the double bonds is not conjugated. Suitable terminal olefinic hydrocarbons may be represented by the general formula $RCH=CH_2$ wherein R is either alkyl, alkenyl, alkadienyl, cycloalkyl, cycloalkenyl or cycloalkadienyl. Examples of suitable mono-olefinic compounds include propylene, 1-butene, 1-pentene, 1-hexene, 1-heptene, 1-octene, 1-decene, 1-hexadecene, 1-octadecene, 1-eicosene, vinyl cyclohexane, and the like. Examples of suitable diolefinic compounds include 1,4-pentadiene, 1,5-hexadiene, 1,9-decadiene, 1,7-octadiene, and the like. Mixtures of terminal olefinic hydrocarbons may also be employed.

Oxygen may be supplied to the reaction either essentially as pure oxygen or admixed with other gases which are substantially inert under the reaction conditions. Air may be used as the source of oxygen if so desired. In common with most organic reactions, the oxidations of the present invention can be exothermic and as a consequence care should be exercised in preventing the formation of explosive oxygen concentrations. The oxygen pressure may suitably be the autogenous pressure at the reaction temperature employed. Alternatively, elevated pressures, suitably in the range from 2 to 250 psig above the autogenous pressure at the reaction temperature may be employed.

As regards the catalyst (a), the palladium, rhodium, ruthenium or iridium constituting component (i) of the catalyst may be in the form of the elemental metal, such as a finely divided powder, or in the form of a compound of the metal. Suitable compounds of the metals include salts, such as the chlorides, iodides, acetates, and complexes of the metals with suitable ligands. Preferably the compound of the metal is a metal halide. Examples of suitable compounds which may be used in the exercise of the invention include palladium (II) chloride, palladium (II) iodide, palladium (II) acetate, palladium (II) acetylacetonate, palladium (II) nitrate tris (triphenylphosphine), ruthenium (II) chloride, ruthenium (III) chloride, ruthenium (111) iodide, ruthenium (III) acetate, rhodium (III) chloride trihydrate, iridium (III) chloride, iridium (III) iodide, iridium (III) acetate, cobalt (II) chloride, cobalt (II) iodide, cobalt (II) acetate and cobalt (III) acetate.

Copper, which constitutes component (ii) of the catalyst (a) may suitably be added as a cuprous or a cupric compound or as a mixture thereof. A wide variety of copper compounds may be used in the process of the invention. Examples of suitable copper compounds include copper (I) acetate, copper (11) acetylacetonate, copper (I) bromide, copper (I) chloride, copper (II) chloride, copper (I) iodide, copper (II) nitrate, and the like.

As regards the ratios of the catalyst (a) components, the atomic ratio of copper component (ii) to metal(s) component (i) may suitably be in the range from 1:1 to 200:1, preferably from 2:1 to 50:1. The molar ratio of olefinic hydrocarbon reactant to the metal(s) component (i) may suitably be in the range from 5:1 to 1000:1, preferably from 10:1 to 250:1.

The diluent (b) comprises at least two liquid phases. Preferably the diluent comprises two liquid phases, one of which may or may not be an aqueous phase. An example of a two phase system in which water is not one of the phases is methanol/dichloromethane. Preferably the diluent comprises two liquid phases, of which one is an aqueous phase. The nonaqueous phase, hereinafter to be referred to as the organic phase, should be inert under the reaction conditions and should be substantially insoluble in the aqueous phase. Suitably the organic solvent comprising the organic phase may be an aliphatic hydrocarbon, a cycloaliphatic hydrocarbon, an aromatic hydrocarbon, an alkyl-substituted aromatic hydrocarbon or a halogenated aromatic hydrocarbon. Examples of suitable organic solvents include benzene, toluene, hexane, cyclohexane, chlorobenzene, bromobenzene, ortho-xylene, para-xylene, meta-xylene, 1,2,4-trichlorobenzene and methylcyclopentane. Mixtures of the aforesaid diluents may be employed if desired. It will be readily apparent to those skilled in the art that the organic solvent should be chosen having regard to the difference in boiling points between the products of the oxidation process and the solvent so as to facilitate separation of the reaction mixture into its different components.

The amounts of aqueous phase and organic phase based on the olefinic hydrocarbon reactant can vary over a wide range, suitably from 20 to 0.2, preferably from 5 to 1, volumes of organic solvent per volume of olefinic hydrocarbon reactant and from 20 to 0.2, preferably from 5 to 1 volumes of water per volume of olefinic hydrocarbon reactant.

The component (c) of the reaction system is a surfactant. Except when component (i) of the catalyst (a) is palladium, the surfactant may be either:

(a) a quaternary ammonium or phosphonium salt of the general formula $(R^1)(R^2)(R^3)(R^4)Y^+X^-$ wherein Y is ammonium or phosphonium, $R^1$, $R^2$, $R^3$ and $R^4$ are independently either alkyl, aralkyl or aryl groups containing from 1 to 20 carbon atoms with the proviso that the sum of the number of carbon atoms in the groups $R^1$, $R^2$, $R^3$ and $R^4$ is in the range from 8 to 20 carbon atoms and wherein $X^-$ is either $Br^-$, $Cl^-$, $I^-$, $F^-$, $R^5CO_2^-$, $QSO_3^-$, $BF_4^-$ or $HSO_4^-$ wherein $R^5$ has the same significance as the aforesaid $R^1$, $R^2$, $R^3$ or $R^4$ and Q is an aryl or alkaryl group having from 6 to 10 carbon atoms. When Y in the aforesaid formula is phosphonium, it is preferred that the sum of the number of carbon atoms in the groups $R^1$, $R^2$, $R^3$ and $R^4$ be in the lower part of the range. Examples of suitable quaternary ammonium salts include cetyltrimethylammonium bromide and dodecyltrimethylammonium chloride. An example of a suitable quaternary phosphonium salt is cetyltrimethylammonium bromide.

(b) an alkali metal alkyl sulphate of the general formula $R^6OSO_3M$ wherein $R^6$ is an alkyl group of from 10 to 20 carbon atoms and M is an alkali metal.

(c) an alkali metal salt of an alkaryl sulphonic acid of the general formula:

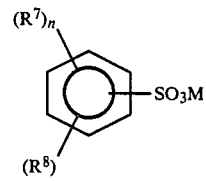

wherein $R^8$ has the same meaning as for $R^6$ hereinabove, $R^7$ is an alkyl group of from 1 to 4 carbon atoms, n is 0 or an integer of from 1 to 4 and M is an alkali metal.

(d) an alkali metal salt of an alkanoic acid of the general formula $R^9CO_2M$ wherein $R^9$ has the same meaning as for $R^6$ hereinabove and M is an alkali metal.

(e) a 1-alkyl pyridinium salt of the general formula:

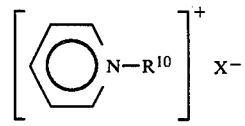

wherein $R^{10}$ has the same meaning as for $R^6$ hereinabove and $X^-$ has the meaning ascribed to $X^-$ in (1) above. When component (i) of the catalyst (a) is palladium, the surfactant may be either dodecyl trimethylammonium chloride or bromide or cetyltrimethylammonium chloride or bromide.

The amount of surfactant (c) can be expressed in terms of a mole ratio based on the metal(s) component (i) of the catalyst (a). Suitably the mole ratio of surfactant to component (i) of the catalyst (a) may be in the range from 0.01:1 to 10:1, preferably from 0.1:1 to 3:1.

In addition to the foregoing there may also be added as component (iii) of the catalyst (a), except when component (i) is palladium, either an alkali metal or an alkaline earth metal chloride. Mixtures of alkali metal and/or alkaline earth metal chlorides may also be employed. The molar ratio of chloride ion derived from the alkali metal or alkaline earth metal chloride to component (i) of the catalyst (a) may suitably be in the range from 5:1 to 1000:1, preferably from 20:1 to 400:1.

As regards the reaction conditions, the process may suitably be operated at a temperature in the range from about 20° to 200° C., preferably from 60° to 150° C. The reaction time may vary over a wide range, suitably from about 30 minutes to 8 hours, though longer reaction times, for example up to 50 hours may be used if desired.

The process may be carried out batchwise or continuously, preferably continuously.

The carbonyl compounds produced by the process of the invention are ketones. Generally, the number of keto-carbonyl groups introduced into the olefinic hydrocarbon will correspond to the number of terminal carbon to carbon double bonds in the olefinic hydrocarbon. Ketones so-formed find use as solvents (e.g. methyl ethyl ketone) and reactive intermediates (e.g. pinacolone).

The invention will now be described in further detail by reference to the following Examples.

EXAMPLE 1

A mixture of copper (II) chloride dihydrate [10 mmol] and palladium (II) chloride [1.0 mmol] in water [10 ml] was stirred for 10 minutes at room temperature. Then 1-decene [3.51 g, 25 mmol] was added followed by benzene [15 ml] and dodecyltrimethylammonium chloride [2.0 mmol]. Oxygen was bubbled through the solution at 80° C. for 48 hours. After cooling to room temperature, ethyl acetate (15 ml) was added and the solution was filtered. The filtrate was dried using anhydrous magnesium sulphate, and then distilled to provide pure 2-decanone in 75% yield and 2-decene in 2% yield.

EXAMPLE 2

The procedure of Example 1 was repeated using 1-butene in place of 1-decene. 2-Butanone was obtained in 68% yield.

EXAMPLE 3

The procedure of Example 1 was repeated using 1,7-octadiene in place of 1-decene. 2,7-octanedione was obtained in 77% yield.

EXAMPLE 4

The procedure of Example 1 was repeated using vinyl cyclohexane in place of 1-decene. The corresponding methyl ketone was obtained.

EXAMPLE 5

The procedure of Example 1 was repeated except that dodecyltrimethylammonium chloride was replaced by cetyltrimethylammonium bromide. 2-Decanone was obtained in good yield.

Comparison Test 1

The procedure of Example 1 was repeated using benzyltriethylammonium chloride in place of dodecyltrimethylammonium chloride. 2-Decene was obtained in high yield. No 2-decanone was observed.

Comparison Test 2

The procedure of Example 1 was repeated using tricaprylmethylammonium chloride in place of dodecyltrimethylammonium chloride. 2-Decene was obtained as the major product.

The results of the Comparison Tests, which are not illustrative of the process of the present invention and are included only for the purpose of comparison, demonstrate the critical role played by the surfactant in determining the nature of the reaction products using palladium as component (i) of the catalyst (a).

EXAMPLE 6

A mixture of copper (11) chloride dihydrate [10 mmol] and tris (triphenylphosphine) ruthenium (11) chloride [1.0 mmol] in water [10 ml] was stirred for 10 minutes at room temperature. Then 1-decene [3.51 g, 25 mmol] was added followed by benzene [15 ml] and dodecyltrimethylammonium chloride [2.0 mmol]. Oxygen was bubbled through the solution at 80° C. for 48 hours. After cooling to room temperature, ethyl acetate (15 ml) was added and the solution was filtered. The filtrate was dried using anhydrous magnesium sulphate, and then distilled to provide pure 2-decanone in 64% yield.

EXAMPLE 7

The procedure of Example 6 was repeated using ruthenium (111) chloride in place of tris (triphenylphosphine) ruthenium (11) chloride. 2-Decanone was obtained in 20% yield.

EXAMPLE 8

The procedure of Example 6 was repeated using rhodium (111) chloride trihydrate in place of tris (triphenylphosphine) ruthenium (11) chloride. 2-Decanone was obtained in 49% yield.

EXAMPLE 9

The procedure of Example 6 was repeated except that 1-butene was used in place of 1-decene. 2-Butanone was obtained.

EXAMPLE 10

The procedure of Example 6 was used except that 1,7-octadiene was used in place of 1-decene. 2,7-Octanedione was obtained.

EXAMPLE 11

The procedure of Example 6 was repeated except that dodecyltrimethylammonium chloride was replaced by cetyltrimethylammonium bromide. 2-Decanone was obtained in good yield.

EXAMPLE 12

The procedure of Example 1 was used except that the benzene/water diluent was replaced by methanol/dichloromethane. The amounts of the reactants were as follows:
Methanol=25 ml
Dichloromethane=10 ml
Copper (11) chloride dihydrate=1.7 g (12.58 mmol)
Palladium (11) chloride=0.15 g (0.84 mmol)
1-Decene=3.51 g (25 mmol)
Dodecyltrimethylammonium chloride=2.0 mmol
Oil bath temperature=45° C.
Oxygen bubbling time=20 hours
2-Decanone was obtained in 83% yield.

We claim:

1. A process for the conversion of a terminal carbon-carbon double bond of an olefinic hydrocarbon having the formula $RCH=CH_2$ wherein R is either alkyl, alkenyl, alkadienyl, cycloalkyl, cycloalkenyl or cycloalkadienyl, to carbonyl groups by reacting the olefin with oxygen in the presence of:
(a) a catalyst comprising
  (i) a metal
  (ii) copper
(b) a diluent comprising at least two liquid phases, and
(c) a surfactant,
wherein the component (i) of the catalyst (a) is one or more of palladium, rhodium, ruthenium or iridium, provided that when the metal is palladium, an alkali metal or alkaline earth metal chloride does not form a component of the catalyst (a) and the surfactant is either dodecyltrimethylammonium chloride or bromide or cetytrimethyllammonium chloride.

2. A process according to claim 1 wherein the olefinic hydrocarbon is an acyclic olefin containing from 3 to 20 carbon atoms per molecule having either 1,2 or 3 terminal olefinic carbon-carbon double bonds per molecule, provided that when there are two or more terminal carbon-carbon double bonds at least one of the double bonds is not conjugated.

3. A process according to claim 1 wherein component (i) of the catalyst (a) is palladium.

4. A process according to claim 1 wherein the component (i) of the catalyst (a) is in the form of a metal halide.

5. A process according to claim 1 wherein the diluent (b) comprises an aqueous phase and an organic phase, the organic phase being an aliphatic hydrocarbon, a cycloaliphatic hydrocarbon, an aromatic hydrocarbon, an alkyl-substituted hydrocarbon or a halogenated aromatic hydrocarbon.

6. A process according to claim 1 wherein the surfactant is selected from:

(a) quaternary ammonium or quaternary phosphonium salts of the general formula $(R^1)(R^2)(R^3)(R^4)Y^+X^-$ wherein Y is ammonium or phosphonium and wherein $R^1$, $R^2$, $R^3$ and $R^4$ are independently either alkyl, aralkyl or aryl groups containing from 1 to 20 carbon atoms with the proviso that the sum of the number of carbon atoms in the groups $R^1$, $R^2$, $R^3$ and $R^4$ is in the range from 8 to 20 carbon atoms and wherein $X^-$ is either $Br^-$, $Cl^-$, $I^-$, $F^-$, $R^5CO_2^-$, $QSO_3^-$, $BF_4^-$ or $HSO)_4^-$ wherein $R^5$ has the same significance as the aforesaid $R^1$, $R^2$, $R^3$ or $R^4$ and Q is an aryl or alkaryl group having from 6 to 10 carbon atoms.

(b) alkali metal alkyl sulphates of the general formula $R^6OSO_3M$ wherein $R^6$ is an alkyl group of from 10 to 20 carbon atoms and M is an alkali metal.

(c) alkali metal salts of alkaryl sulphonic acids of the general formula:

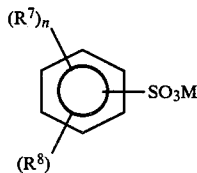

wherein $R^8$ has the same meaning as for $R^6$ hereinabove, $R^7$ is an alkyl group of from 1 to 4 carbon atoms, n is 0 or an integer of from 1 to 4 and M is an alkali metal.

(d) alkali metal salts of an alkanoic acid of the general formula $R^9CO_2M$ wherein $R^9$ has the same meaning as for $R^6$ hereinabove and M is an alkali metal.

(e) 1-alkyl pyridinium salts of the general formula:

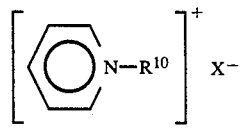

wherein $R^{10}$ has the same meaning as for $R^6$ hereinabove and $X^-$ has the meaning ascribed to $X^-$ in (1) above.

7. A process according to claim 1 wherein in the catalyst (a) the atomic ratio of component (ii) to component (i) is in the range from 2:1 to 50:1 and the molar ratio of olefinic hydrocarbon reactant to component (i) is in the range from 10:1 to 250:1, in the diluent (b) the amount of organic phase is in the range from 5 to 1 volumes of organic phase per volume of olefinic hydrocarbon reactant and the amount of aqueous phase is from 5 to 1 volumes of water per volume of olefinic hydrocarbon reactant and the mole ratio of surfactant (c) to component (i) of the catalyst (a) is in the range from 0.1:1 to 3:1.

8. A process according to claim 1 wherein the catalyst (a) contains as an additional component (iii) either an alkali metal or an alkaline earth metal chloride in an amount such that the molar ratio of chloride ion derived therefrom to component (i) of the catalyst (a) is in the range from 20:1 to 400:1.

9. A process according to claim 1 wherein the temperature is in the range from 20° to 200° C.

10. A process for the conversion of a terminal carbon-carbon double bond of an olefinic hydrocarbon to carbonyl groups by reacting the olefin with oxygen in the presence of:

(a) a catalyst comprising
   (i) a metal
   (ii) copper
a diluent comprising at least two liquid phases, and
(c) a surfactant,
wherein the component (i) of the catalyst (a) is one or more of rhodium, ruthenium or iridium, and
wherein the olefinic hydrocarbon is an acyclic olefin containing from 3 to 20 carbon atoms per molecule having either 2 or 3 terminal olefinic carbon-carbon double bonds per molecule, provided that when there are two or more terminal carbon-carbon double bonds at least one of the double bonds is not conjugated.

11. A process according to claim 10 wherein said olefinic hydrocarbon is a diolefinic compound selected from the group consisting of 1,4-pentadiene, 1,5-hexadiene, 1,9-decadiene and 1,7-octadiene.

12. A process according to claim 11 wherein said diolefinic compound is 1,7-octadiene.

13. A process for the conversion of a terminal carbon-carbon double bond of an olefinic hydrocarbon to carbonyl groups by reacting the olefin with oxygen in the presence of:

(a) a catalyst comprising
   (i) a metal
   (ii) copper
(b) a diluent comprising at least two liquid phases, and
(c) a surfactant,
wherein the component (i) of the catalyst (a) is one or more of rhodium, ruthenium or iridium.

* * * * *

UNITED STATES PATENT AND TRADEMARK OFFICE
CERTIFICATE OF CORRECTION

PATENT NO. : 4,568,770

DATED : February 4, 1986

INVENTOR(S) : HOWARD ALPER, KRZYSZTOF R. JANUSZKIEWICZ and DAVID J.H. SMITH

It is certified that error appears in the above-identified patent and that said Letters Patent are hereby corrected as shown below:

Col. 7, line 26, claim 6, "HSO)$_4$" should read --HSO$_4$--

Col. 8, line 31, claim 10, Before "a diluent comprising" --(b)-- has been omitted.

Signed and Sealed this

Twentieth Day of May 1986

[SEAL]

Attest:

DONALD J. QUIGG

Attesting Officer

Commissioner of Patents and Trademarks